US005942627A

United States Patent [19]

Lemke

[11] Patent Number: 5,942,627
[45] Date of Patent: Aug. 24, 1999

[54] CONCENTRATED AMPHOCARBOXYLPROPIONATE SURFACTANTS PRODUCED FROM METHYL ACRYLATE AND 2-ALKYL IMIDAZOLINE

[75] Inventor: Daniel Wayne Lemke, Jersey Shore, Pa.

[73] Assignee: Lonza Inc., Fair Lawn, N.J.

[21] Appl. No.: 08/829,079

[22] Filed: Mar. 31, 1997

[51] Int. Cl.$^6$ .......................... C07D 233/18; C07D 233/26; C07D 233/28; B01F 17/00

[52] U.S. Cl. .......................................... 548/352.1; 252/357

[58] Field of Search ........................... 548/352.1; 252/357

[56] References Cited

U.S. PATENT DOCUMENTS

| | | | |
|---|---|---|---|
| 2,773,068 | 12/1956 | Mannheimer | 548/352.1 |
| 2,781,349 | 2/1957 | Mannheimer | 548/352.1 |
| 2,781,350 | 2/1957 | Mannheimer | 548/352.1 |
| 2,781,351 | 2/1957 | Mannheimer | 548/352.1 |
| 2,820,043 | 1/1958 | Rainey et al. | 548/352.1 |
| 2,889,193 | 6/1959 | Denman et al. . | |
| 2,947,703 | 8/1960 | Larsonneur . | |
| 3,187,003 | 6/1965 | McBride, Jr. et al. . | |
| 3,555,041 | 1/1971 | Katz . | |
| 4,137,245 | 1/1979 | Christiansen et al. | 548/352.1 X |
| 4,238,499 | 12/1980 | Lover et al. | 548/352.1 X |
| 4,362,737 | 12/1982 | Schafer et al. | 548/352.1 X |
| 4,431,672 | 2/1984 | Yamada et al. | 424/353 |
| 4,720,383 | 1/1988 | Drach et al. | 424/70 |
| 4,954,635 | 9/1990 | Rosario-Jansen et al. | 548/352.1 |
| 5,322,640 | 6/1994 | Byrne et al. | 252/389.22 |

FOREIGN PATENT DOCUMENTS

| | | | |
|---|---|---|---|
| 51-56447 | 5/1976 | Japan | 548/352.1 |
| 1078101 | 11/1964 | United Kingdom . | |

OTHER PUBLICATIONS

Sales literature, Lonza, Inc., Specialty Chemicals, 1 page.

Chemical Abstract, vol. 117: 114048m, 1992, p. 132.

Abstract, 65: 3652d & 57:5700f, 1 page.

Hein et al., Amphoteric Surfactants—The structure of salt–free amphoteric surfactants, Cosmetics & Toiletries, vol. 95, Nov. 1980, 4 pages.

Technical and Product Development Data, Miranol Products for Household Industrial Applications, cover page and pp. 1–51.

*Primary Examiner*—Floyd D. Higel
*Attorney, Agent, or Firm*—Darby & Darby

[57] ABSTRACT

A method for producing amphocarboxylpropionate comprising initiating the reaction of methyl acrylate with 2-alkyl imidazoline in the substantial absence of water; adding from 0.3 to 2 moles of water per mole of 2-alkyl imidazoline to the reaction products after at least 1.3 moles of the methyl acrylate reacts with one mole of the 2-alkyl imidazoline, so as to form a reaction product having a molar ratio of at least 1.8:1 of methyl acrylate to imidazoline. The products of the method can be formulated in highly concentrated form and do not have the gelling problems of the prior art formulation. These products are useful and beneficial in personal care products.

24 Claims, No Drawings

CONCENTRATED AMPHOCARBOXYLPROPIONATE SURFACTANTS PRODUCED FROM METHYL ACRYLATE AND 2-ALKYL IMIDAZOLINE

BACKGROUND OF THE INVENTION

Amphocarboxylpropionate surfactants are amphoteric compounds that are the reaction products of 2-alkyl imidazoline, methyl acrylate, alkali metal hydroxide, and water. They are sodium chloride free. Therefore, the surfactant of its own accord will build or reduce the viscosity of a formulation. This then allows the formulator the option to control viscosity with whatever he chooses, without having to be concerned about the level of salt in the surfactant and the subsequent influence on viscosity building. They are excellent hydrotroping agents and are very useful as low irritancy additives in personal care formulations, such as baby shampoos, hand soaps, and dish soaps.

Amphocarboxylpropionate surfactants are commonly sold as a 40:54:6 (by weight) mixture of amphoteric:water:methanol. The methanol is present as a saponification by-product. In some cases it can be removed and in other cases it is removed and substituted with another alcohol such as ethanol, isopropanol, and propylene glycol. Sodium acrylate is also present as the result of saponified unreacted methyl acrylate and usually constitutes about 4–8% of the non-aqueous portion of the product. It is an undesirable by-product and adds nothing to a formulation.

Transporting and storing a product containing such a low concentration of active, however, is expensive and inconvenient.

Mixtures of 72:19:9 wt. % amphoteric:water:methanol and amphoteric:water:propylene glycol are also commercially available. However, they are highly viscous and tend to gel, both in their concentrated form and when added to an aqueous medium at temperatures lower than 70° C. If not mixed during storage, a thick gelatinous material forms on the surface.

There is therefore a need for an amphocarboxylpropionate surfactant that can be highly concentrated, so as to save costs associated with storage and shipping, which is low in residual metal acrylate. In addition, there is a need for concentrated aqueous amphocarboxylpropionate solutions that do not gel when stored in the absence of stirring, or when diluted with water.

SUMMARY OF THE INVENTION

In one aspect, the present invention relates to an improved method for producing an amphocarboxylpropionate surfactant. Conventionally, these compounds are prepared by combining methyl acrylate with 2-alkyl imidazoline (1-hydroxyethyl, 2-alkyl imidazoline) in a water-free process. The reaction product is then saponified with an alkali metal hydroxide. The improvement of the present invention comprises adding a controlled amount of water after the methyl acrylate/2-alkyl imidazoline reaction has begun, preferably after the reaction of at least 1.3 moles of methyl acrylate with each mole of 2-alkyl imidazoline. Unexpectedly, the water addition allows for the further reaction of the methyl acrylate and 2-alkyl imidazoline, resulting in a product having a higher methyl acrylate to 2-alkyl imidazoline ratio than would otherwise be attainable. In addition, the product can be obtained in a more concentrated form than was heretofore possible without the gelling problems of the conventional amphocarboxylpropionate surfactant.

In another aspect, the invention relates to an amphocarboxylpropionate surfactant comprising the reaction product of methyl acrylate and 2-alkyl imidazoline in a molar ratio of about 1.8–2.4:1.0. The surfactant is preferably in aqueous solution at a concentration greater than about 75 wt. %.

A further aspect of the invention is a solution comprising saponified amphocarboxylpropionate and polyethylene glycol. In such a solution, it has been discovered that the polyethylene glycol prevents a concentrated form of saponified amphocarboxylpropionate from gelling during dilution.

The invention also relates to an aqueous solution containing saponified amphocarboxylpropionate surfactant with less than about 0.5 wt. % of alkaline metal acrylate based on the weight of the non-volatile components of the solution. The amphocarboxylpropionate used in making such solution is the reaction product of methyl acrylate and 2-alkyl imidazoline in a ratio of less than about 1.7:1.

DETAILED DESCRIPTION OF THE INVENTION

The amphocarboxylpropionate surfactant of the invention has several advantages over conventional amphocarboxylpropionate surfactant. It can be made into a much more concentrated solution. This property results from a higher ratio of reacted methyl acrylate to 2-alkyl imidazoline than is found in conventional amphocarboxylpropionates. This increase in the ratio of methyl acrylate to 2-alkyl imidazoline results from the addition of water after the reaction of at least 1.3 moles of the methyl acrylate with the 2-alkyl imidazoline. Addition of water is believed to result in hydrolytic degradation of the imidazolinium ring formed in the reaction product of methyl acrylate and 2-alkyl imidazoline, creating reactive amine sites which combine with free methyl acrylate in solution. The ratio of reacted methyl acrylate to 2-alkyl imidazoline in the amphocarboxylpropionate, which in conventional amphocarboxylpropionate surfactant is about 1.6 or less, is raised to between about 1.8 and about 2.4, the latter being the theoretical maximum ratio based on the theorized mechanism of this reaction. To minimize residual methyl acrylate, and maximize the advantages of this invention, the ratio of reacted methyl acrylate to 2-alkyl imidazoline is preferably between about 2.2 and 2.4.

This invention also provides amphocarboxylpropionate that can be stored without gelling or surface filming. Also, when diluted, e.g., with an equal volume of water at room temperature, the amphocarboxylpropionate of the invention does not gel.

The level of residual alkali metal hydroxide acrylate, e.g., sodium acrylate, that remains in the amphocarboxylpropionate surfactant of the invention is lower than that for conventional amphocarboxylpropionate surfactant. In the conventional surfactant, unreacted alkali metal acrylate cannot be removed. The lower level of residual acrylate obtained according to the invention results from adding a controlled amount of water prior to saponification. This advantage is achieved both for the novel amphocarboxylpropionate having a methyl acrylate to 2-alkyl imidazoline ratio greater than about 1.8, and for amphocarboxylpropionate having a lower ratio. Specifically, the lower levels of residual acrylate are achieved by the process of the invention when between about 1 and 2.4 moles of methyl acrylate are reacted per mole of 2-alkyl imidazoline. For example, at a molar ratio of less than 1.6, the residual alkali metal acrylate is less than about 0.5 wt. %, based on the weight of the non-volatile components of the solution.

Amphocarboxylpropionates are typically sold with the methyl esters saponified, i.e., converted to alkaline metal salts. This is generally accomplished by adding aqueous sodium hydroxide and heating to 90° C. The partially saponified amphocarboxylpropionates of the invention that are formed from about 1.7–2.4 moles of methyl acrylate for each mole of 2-alkyl imidazoline do not gel when blended rapidly with room temperature water, such as occurs during normal usage. Although commercial amphoterics of this type are usually fully saponified, the amphocarboxylpropionate of the invention has been found to have acceptable properties at a level of about 60 to 80% saponified ester.

At a higher level of saponification, e.g., a molar ratio of alkali metal hydroxide:2-alkyl imidazoline of greater than about 1.6:1, some gelling may occur when mixing rapidly with water. It has been determined, however, that the addition of relatively low concentrations of polyethylene glycol, namely, from 1 to 5 wt. % of the solution, preferably from 2 to 4 wt. %, prevents such gelling. Thus, while normally slight gelling occurs at about 75% saponified ester, and more gelling normally occurs at greater than about 80% saponified ester, this tendency to gel is eliminated by addition of an effective amount of polyethylene glycol. Adding polyethylene glycol has also been found to reduce gelling that occurs in conventional saponified, or partially saponified, amphocarboxylpropionate surfactants, i.e., those containing less than 1.7 moles of reacted methyl acrylate for each mole of 2-alkyl imidazoline and more than 75% of the concentrated form.

The amphocarboxylpropionate of the invention is, as stated above, formed from methyl acrylate and 2-alkyl imidazoline. The alkyl group of the 2-alkyl imidazoline may be straight or branched chain and contain from 6 to 20 carbon atoms. The commercially available 2-alkyl imidazoline is typically made by reacting a fatty acid and aminoethylethanolamine. They are readily prepared by the procedure described by Mannheimer in U.S. Pat. No. 2,773,068. The preferred fatty acid for use in personal care formulations is coconut fatty acid.

Ethyl hexanoic acid, blends of octanoic and decanoic acid, lauric acid, palm kernel fatty acid, palmitic acid, oleic acid, tall oil fatty acid, and stearic acid are a few of the other fatty acids that are used by the surfactant industry to prepare 2-alkyl imidazoline. While the subject application is directed to the 2-substituted imidazolines, this heterocyclic ring, as is well known to those skilled in the art, may be substituted at other positions on the ring.

In addition to those mentioned above, other acrylates, such as ethyl or propyl, and other low molecular weight alkyl esters can also be used in the practice of the invention and yield the same benefits as described herein.

While the propionates are commonly used in the personal care market, the teaching of the invention would also apply to other amphocarboxyl carboxylates, e.g., butylates and ethylates.

The reaction between methyl acrylate and 2-alkyl imidazoline is broadly carried out at a temperature of between about 30° and 110° C., preferably between 60° and 90° C., at a pressure broadly between about 0 and 50 psig, preferably between 0 and 30 psig, for a period of between 2 and 24 hours, preferably between 5 and 8 hours. The molar ratio of the reactants varies, dependent on the specific product being prepared. However, broadly from 1:0 to 1:2.5, preferably from 1:1.3 to 1:2.4, should be used.

The controlled amount of water is added to the reaction after the addition of the 1.3 moles of methyl acrylate, and preferably after the addition of about 1.6 moles, for every mole of 2-alkyl imidazoline. Based on kinetic studies, the controlled amount of water should be added to the reaction product within 2 to 24 hours after the initiation of the addition reaction, preferably between 4 and 18 hours, and most desirably within 5 to 8 hours. From 0.3 to 2 moles of water per mole of 2-alkyl imidazoline are added, preferably from 0.6 to 1.0. While somewhat more water can be added, this is generally not preferred, since excess water appears to terminate the reaction prematurely.

The preferred surfactant of the invention is disodium cocoamphodipropionate. For specific applications, however, the potassium salts and the free acid forms may also be used. However, the sodium salts are the most common and sought-after amphoterics.

The surfactant of the invention can form highly stable foam and provide good surface tension reduction and electrolyte tolerance. It may be used in cleaning formulations, e.g., hard surface and heavy duty cleaning formulations, and personal care formulations, including detergents for hair and skin. The surfactant of the invention is particularly well suited for formulations having a high concentration of the active ingredient where high viscosity is undesirable.

The present invention is illustrated by the following examples. These examples are intended to exemplify this invention, not to limit its scope.

EXAMPLE 1

Study of Methyl Acrylate/2-alkyl Imidazoline Reaction Without Addition of Water Prior to Saponification Studies were carried out with respect to the methyl acrylate/2-alkyl imidazoline reaction made according to the prior art, i.e., without addition of water to increase the amount of acrylate reacted. The methyl acrylate (MAC) and 2-alkyl imidazoline were added in a 2:1 molar ratio.

The 2-alkyl imidazoline was charged (215.5 g, 0.7808 mol) into a 500 ml four-neck flask fitted with a thermometer, temperature controller, mechanical stirrer and high efficiency water-cooled condenser and heated to reaction temperature. Methyl acrylate, (134.5 g, 1.562 mol) was added rapidly through an addition funnel to the imidazoline. The methyl acrylate and 2-alkyl imidazoline were combined in a 2:1 molar ratio. The same temperature was maintained throughout the duration of the reaction.

The following table shows the reaction parameters for the addition of methyl acrylate:

TABLE 1

| REACTION NO. | REACTION TEMP (° C.) | MOLES OF MAC REACTED AFTER 6 HRS. |
|---|---|---|
| 1 | 30 | 1.03 |
| 2 | 50 | 1.42 |
| 3 | 60 | 1.43 |
| 4 | 70 | 1.54 |
| 5 | 80 | 1.61 |

These results show that the conventional reaction, i.e., without adding the controlled amount of water, did not result in reaction of more than about 1.6 moles of methyl acrylate for every mole of 2-alkyl imidazoline. Similar experiments were carried out at higher temperatures and pressures; still no more than about 1.6 moles of methyl acrylate for every mole of 2-alkyl imidazoline reacted. Kinetic analysis showed that the first mole of methyl acrylate reacted approximately twelve times faster than the second mole.

EXAMPLE 2

Study of Methyl Acrylate/2-alkyl Imidazoline Reaction With Addition of Water To illustrate the advantages of the present invention, experiments were carried out in which methyl acrylate and the 2-alkyl imidazoline of Example 1 were combined, with water being added after the initial reaction commenced.

2-alkyl imidazoline (739 grams, 2.68 moles) and methyl acrylate (461 grams, 5.35 moles) were charged into a two-liter four-neck flask fitted with a thermometer, a temperature controller, mechanical stirrer, and a water cooled condenser. The mixture was heated carefully to 80° C. and maintained at that temperature. After six hours, the mixture was sampled for percent residual methyl acrylate. It was estimated that approximately 1.6 moles of the methyl acrylate has reacted at this time. A controlled amount of water (29.2 grams, 1.62 moles) was then added. This amount is equivalent to 0.6 mole of water per mole of 2-alkyl imidazoline. The 80° C. temperature was maintained and the mixture sampled periodically as shown in Table 2 below. When the percentage of residual methyl acrylate ceased to change, 50% sodium hydroxide (236 grams, 2.95 moles) was slowly added over a two-hour period to saponify the product.

Additional runs were carried out at the molar ratios and temperatures indicated in Table 2. The molar ratio of methyl acrylate (MAC) to 2-alkyl imidazoline (2-AI) in the feed is shown ("MOL. RAT. MAC/2-AI").

TABLE 2

| | REAC. | MOL. RAT. | MOLES WATER/ | WT. % RESIDUAL MAC BASED ON HPLC | | | |
|---|---|---|---|---|---|---|---|
| NO REF. | TEMP (° C.) | MAC/2-AI IN FEED | MOLE 2-AI | 6 HRS* | 10 HRS | 16 HRS | 18 HRS |
| A | 60 | 1.30 | 0.6 | 4.8 | 0.23 | | |
| B | 60 | 1.60 | 0.6 | 4.3 | | 0.5 | |
| C | 60 | 1.65 | 0.6 | 7.4 | 1.3 | 0.61 | |
| D | 60 | 2.0 | 0.6 | 8.4 | 0.9 | 0.8 | |
| E | 60 | 2.0 | 0.8 | 9.2 | 1.0 | | 0.7 |
| F | 80 | 2.0 | 0.4 | 10.4 | 2.1 | | |
| G | 80 | 2.0 | 0.8 | 6.7 | 1.5 | 1.2 | |
| H | 80 | 2.4 | 0.9 | 8.2 | 4.7 | 3.8 | 3.5 |
| I | 60 | 2.5 | 0.8 | 8.0 | | | 3.3 |

*Analysis taken just prior to the addition of water.

These results show that the addition of water decreased the unreacted methyl acrylate in the reaction product. According to the mechanism hypothesized for the reaction, the product obtained contained close to the maximum theoretical ratio of reacted methyl acrylate to 2-alkyl imidazoline.

EXAMPLE 3

Effects on Gelling Properties of Varying the Degree of Saponification of Product of the Invention Experiments were carried out to determine what effect the degree of saponification has on gelling properties of the product of the invention. The product had a molar ratio of reacted methyl acrylate to 2-alkyl imidazoline of about 2.4:1.

2-alkyl imidazoline (1,930 grams, 6.99 moles) and methyl acrylate (1,445 grams, 16.78 moles) were charged into a five-liter four-neck flask fitted with a thermometer, a temperature controller, mechanical stirrer, and a water cooled condenser. The mixture was heated to 80° C. and maintained at that temperature. After six hours, water (113 grams, 6.292 moles) was added. When the percent of residual methyl acrylate was <2% sodium hydroxide (50% aq., 783 grams, 9.786 moles) was slowly added over a two-hour period. The product was sampled for odor, percent methanol (by gas chromatography), pH (at 10% in water), and for its tendency to gel when combined with an equal amount of water (see Table below). "M/R NaOH:2-AI" refers to the molar ratio of NaOH to 2-alkyl imidazoline that was added. "Typical amphoteric" odor is the acceptable odor for commercially available amphoteric products. Additional runs were conducted at the molar ratio of NaOH:2-alkyl imidazoline shown ("M/R NaOH:2-AI").

TABLE 3

| REF. NO. | M/R NaOH:2-AI | METHANOL WT. % | SAPONIFIED ESTER* WT. % | pH (10% IN WATER) | ODOR | TENDENCY TO GEL |
|---|---|---|---|---|---|---|
| AA | 1.0 | 6.5 | 49 | 9.7 | acrylate like | no |
| AB | 1.2 | 6.6 | 51 | 9.7 | acrylate like | no |
| AC | 1.4 | 9.4 | 77 | 9.9 | slight | no |
| AD | 1.6 | 9.4 | 77 | 9.9 | slight | slight |
| AE | 2.0 | 9.8 | 84 | — | typical amphoteric | yes |
| AF | 2.2 | 9.8 | 86 | 11.2 | typical amphoteric | yes |

*Calculated based upon the amount of methanol present.

These results showed that a product of the invention having a level of saponification of between 75 and 80% exhibited no or only slight gelling and had an acceptable odor.

EXAMPLE 4

Reduction of Gelling by Addition of Polyethylene Glycol

A series of concentrated amphocarboxylpropionates was prepared by adding methyl acrylate to imidazoline in molar ratios that varied from 1.3 to 2:1. Additives were combined with the amphocarboxylpropionate to dilute the wt. % actives to 80%. The amount of each additive was between about 3 and 5 wt. %. The mixture of additive and amphocarboxylpropionate was then combined with cold water in a 50:50 blend and the tendency for the amphoteric to gel was determined. The additives evaluated were: propylene glycol, hexylene glycol, glycerol, polyglycerol (di and hexa), lauryl alcohol, ceteth-20, and polyethylene glycol (PEG 200, 300, and 600).

Only the polyethylene glycols reduced the tendency to gel when the amphocarboxylpropionate mixture was combined with water.

EXAMPLE 5

Measurement of Physical and Performance Properties of Surfactants of the Invention Amphocarboxylpropionate surfactants of various ratios of reacted methyl acrylate:2-alkyl imidazoline, and a sample containing polyethylene glycol, were prepared and evaluated for viscosity at various concentrations, Draves wetting, and hydrotrope strength (see Table below). They were compared with two commercially available amphoteric surfactants, Amphoterge® and Amphoterge® K-2 (Lonza Inc.). The active ingredients in these products are sodium cocoamphopropionate and disodium cocoamphodipropionate, respectively.

TABLE 4

| REF. | M/R MA/IMID | DRAVES WETTING 1%, SEC. | HYDROTROPE STRENGTH GRAM SURFACTANT PER GRAM SUBSTRATE | VISCOSITY CPS THOUSANDS 83% ACTIVES | VISCOSITY CPS THOUSANDS 40% ACTIVES |
|---|---|---|---|---|---|
| AMPHOTERGE ® K 40% ACTIVE | 1.4 | 75 | 0.68 | — | 0.3 |
| AMPHOTERGE ® K-2 40% ACTIVE | 2.0 | 245 | 0.60 | — | .080 |
| BA | 1.3 | 100 | 0.63 | 44 | GEL |
| BA and 3% PEG 300 | 1.3 | — | — | 40 | .355 |
| BC | 1.6 | 180 | 0.58 | 70 | .230 |
| BD | 2.0 | 250 | 0.60 | 86 | .230 |
| BE | 2.25 | — | 0.60 | 30 | .150 |
| BF | 2.5 | 175 | 0.60 | 20 | .160 |

The above data show that the concentrated product of the invention performs the same as the standard amphocarboxylic propionates on an equivalent weight actives level. This is seen by the comparable wetting and hydrotrope results (columns 3 and 4 above).

Furthermore, the concentrate when diluted to 40% is indistinguishable from the standard 40% actives product in performance and in appearance.

Accordingly, the concentrated amphoteric of the invention can be used as a direct substituent for the standard 40% active solution, while at the same time reducing the formulation inventory by half and eliminating the filming over during storage and gelling out during dilution, both of which are common to the prior art commercial concentrates.

EXAMPLE 6

Evaluation of Formulations Prepared from Surfactant of the Invention

Two formulations were prepared from a surfactant of the invention made from added methyl acrylate:2-cocoimidazoline in a 2.25:1 ratio. The formulations are shown in the following table:

TABLE 5

| INGREDIENTS | DISH WASH | FINE FABRIC WASH |
|---|---|---|
| Amphocarboxylpropionate of the invention | 8.0 | 4.0 |
| Carsonal ™ SES-S[1] | 20.0 | — |
| Carsonal ™ SLES-3[2] | — | 30.0 |
| Carsamide ™ CA[3] | 4.0 | — |
| Carsamide ™ SAL-9[4] | — | 4.0 |
| Barlox ™ 12[5] | 2.0 | — |
| Citric acid (50%) | 2.4 | — |
| Tinopal ™ SWN[6] | — | 0.1 |
| Water | 63.6 | 61.9 |
| Total | 100.0 | 100.0 |

[1]Sodium laureth sulfate (60%)
[2]Sodium laureth sulfate (30%)
[3]Cocamide DEA
[4]Lauramide DEA
[5]Cocamide oxide
[6]Optical brightener The formulations were compared with formulations containing Amphoterge® K-2 for pH, viscosity, and for phase stability, as shown in the following table:

TABLE 6

| | DISH WASH | | FINE FABRIC WASH | |
|---|---|---|---|---|
| | AMPHOTERGE ® K-2 | AMPHOTERIC OF THE INVENTION | AMPHOTERGE ® K-2 | AMPHOTERIC OF THE INVENTION |
| pH | 6.4 | 6.1 | 9.3 | 9.2 |
| Viscosity (cps) | 20 | 40 | 5 | 5 |
| Phase Stability | Pass | Pass | Pass | Pass |

The above data show the most basic characteristics of the formulations (i.e., pH, viscosity, or phase stability) and the effect of substituting the product of the invention in place of a standard amphoteric. Clearly, the integrity of two types of household formulations was retained.

EXAMPLE 7

Irritancy Tests

Irritancy tests were run on a surfactant of the invention containing 30% unsaponified ester, and on a commercially available amphocarboxylpropionate surfactant (Amphoterge® K-2) containing no unsaponified surfactant. A Bovine Cornea Opacity Permeability (BCOP) test was used to determine the level of irritancy at an active level of 30% for each sample. A higher score indicates higher irritancy. Each score in the Table below represents the average of three data points. The difference seen between the two surfactants was insignificant.

TABLE 7

| TEST SAMPLE | % UNSAPONIFIED ESTER | BCOP SCORE |
|---|---|---|
| Amphoterge ® K-2 | 0 | 6 |
| Product of Invention | 30 | 5 |

It is believed that it is the increase in the level of unsaponified ester and the level of MAC reacted with the 2-alkyl imidazoline that allows the product of the invention to be non-gelling when diluted from a concentrated form and non-filming when stored. However, since one of the most basic benefits of using an amphoteric is that it mitigates the irritancy of a formulation, it was necessary to determine whether the unsaponified esters would change the formulations' irritancy. The BCOP results show that using the formulation of the invention does not change the irritative level of the amphoteric.

What is claimed is:

1. A method for producing an amphocarboxylpropionate comprising reacting at least 1.3 moles of methyl acrylate with one mole of 2-alkyl imidazoline in the substantial absence of water, said alkyl group having from 6 to 20 carbon atoms; admixing from 0.3 to 2 moles of water per mole of 2-alkyl imidazoline with the products of said reaction; and then reacting methyl acrylate with said admixture to form an amphocarboxylpropionate having a molar ratio of at least 1.8:1 of methyl acrylate to imidazoline.

2. The method of claim 1 wherein the water is added after the reaction between the methyl acrylate and the 2-alkyl imidazoline has substantially slowed, said water addition resulting in the reaction of additional methyl acrylate with said reaction product.

3. The method of claim 1 wherein the molar ratio of the water to the 2-alkyl imidazoline is from 0.6 to 1.

4. The method of claim 1 wherein the reaction is initiating by admixing from 1.3 to 2.5 moles of methyl acrylate with each mole of 2-alkyl imidazoline.

5. The method of claim 1 wherein said alkyl group is a coconut derivative.

6. The method of claim 1 wherein said amphocarboxylpropionate is cocoamphocarboxylpropionate.

7. The method of claim 1 further wherein said amphocarboxylpropionate is saponified following the addition of water.

8. A surfactant comprising an amphocarboxylpropionate that is the reaction product of methyl acrylate and 2-alkyl imidazoline, said alkyl group having from 6 to 20 carbon atoms, wherein said reaction product contains reacted methyl acrylate and 2-alkyl imidazole in a molar ratio of about 1.8:1–2.4:1.

9. The surfactant of claim 8 wherein said reaction product contains reacted methyl acrylate and 2-alkyl imidazole in a molar ratio of from about 2.2 to about 2.4.

10. The surfactant of claim 8 comprising less than about 4 wt. % residual alkali metal acrylate based on amphocarboxylpropionate.

11. An aqueous solution comprising the amphocarboxylpropionate of claim 8 in a concentration greater than about 75 wt. %.

12. The aqueous solution of claim 8 wherein said amphocarboxylpropionate is saponified with an alkali metal hydroxide.

13. An aqueous solution comprising an amphocarboxylpropionate and from 1 to 5 wt. % of polyethylene glycol.

14. The aqueous solution of claim 13 wherein said amphocarboxylpropionate is substantially completely saponified.

15. The aqueous solution of claim 13 wherein said amphocarboxylpropionate is the reaction product of methyl acrylate and 2-alkyl imidazoline, wherein said amphocarboxylpropionate is saponified with at least 1.6 moles of alkali metal hydroxide per mole of 2-alkyl imidazoline and wherein said amphocarboxylpropionate is formed by the reaction of about 1.6 to 2.4 moles of methyl acrylate with each mole of 2-alkyl imidazoline.

16. The aqueous solution of claim 15 wherein said amphocarboxylpropionate is saponified with 2 moles of alkali metal hydroxide for each mole of 2-alkyl imidazoline.

17. The aqueous solution of claim 13 having a concentration of amphocarboxylpropionate greater than about 80 wt. %.

18. The aqueous solution of claim 13 wherein said amphocarboxylpropionate is formed by the reaction of from 1 to 1.6 moles of reacted methyl acrylate for each mole of 2-alkyl imidazole.

19. An aqueous solution comprising (1) at least 50% of the saponified reaction product of methyl acrylate and 2-alkyl imidazoline, said alkyl group having from 6 to 20 carbon atoms, wherein said reaction product is formed by reacting greater than 1.3 and less than 1.7 moles of methyl acrylate with each mole of 2-alkyl imidazole and (2) less than about 0.5 wt. % alkaline metal acrylate based on the nonaqueous components of said solution.

20. The aqueous solution of claim 19 wherein said 2-alkyl imidazoline is 1-hydroxyethyl, 2-cocoimidazoline.

21. A method for producing amphocarboxylpropionate comprising:

a) reacting methyl acrylate with 2-alkyl imidazoline in the substantial absence of water at a temperature between 30 and 110° C. and a pressure between 0 and 50 psig until the reaction between the methyl acrylate and the 2-alkyl imidazoline has substantially slowed, wherein said alkyl group has from 6 to 20 carbon atoms; and b) admixing from 0.3 to 2 moles of water per mole of 2-alkyl imidazoline with the reaction products and reacting methyl acrylate with said admixture to form an amphocarboxylpropionate having a molar ratio of between 1.8:1 and 2.5:1 of methyl acrylate:imidazoline.

22. The method of claim 21 wherein said reaction takes place at between 60° C. and 90° C. at a pressure between 0 and 30 psig.

23. The method of claim 22 wherein said water is added at from 4 to 18 hours following initiation of the reaction.

24. The method of claim 23 wherein from 0.6 to 1.0 moles of water are added.

* * * * *